United States Patent
Kunz

(10) Patent No.: US 9,707,065 B2
(45) Date of Patent: Jul. 18, 2017

(54) URINARY INCONTINENCE DEVICE

(75) Inventor: Kenneth Kunz, Delta (CA)

(73) Assignee: Life360 Innovations Inc., Vancouver (CA)

( * ) Notice: Subject to any disclaimer, the term of this patent is extended or adjusted under 35 U.S.C. 154(b) by 149 days.

(21) Appl. No.: 12/845,603

(22) Filed: Jul. 28, 2010

(65) Prior Publication Data

US 2011/0028778 A1 Feb. 3, 2011

Related U.S. Application Data

(60) Provisional application No. 61/229,432, filed on Jul. 29, 2009.

(51) Int. Cl.
*A61F 2/00* (2006.01)

(52) U.S. Cl.
CPC ............ *A61F 2/0009* (2013.01); *A61F 2/005* (2013.01); *A61F 2/0013* (2013.01); *A61F 2/0022* (2013.01); *A61F 2250/0039* (2013.01)

(58) Field of Classification Search
CPC ........ A61F 2/00; A61F 2/0009; A61F 2/0022; A61F 2/0013; A61F 2/0018; A61F 2/0027; A61M 31/00; A61B 2017/00805
USPC ....... 600/32, 29–31; 604/19, 93.01; 128/885
See application file for complete search history.

(56) References Cited

U.S. PATENT DOCUMENTS

| | | |
|---|---|---|
| 2,649,854 A | 8/1953 | Salm |
| 2,848,998 A * | 8/1958 | Bryan ........................... 604/192 |
| 3,463,141 A | 8/1969 | Mozolf |
| 3,648,683 A | 3/1972 | Brodie |
| 4,457,299 A | 7/1984 | Cornwell |
| 4,934,999 A * | 6/1990 | Bader ............................ 600/29 |

(Continued)

FOREIGN PATENT DOCUMENTS

| | | |
|---|---|---|
| DE | 10304614 A1 | 8/2004 |
| EP | 0193406 A2 | 9/1986 |

(Continued)

OTHER PUBLICATIONS

Dribblestop® Product information downloaded from http://www.incontinenceclannp.com/product.php?gclid=CLHvua-Wj6USFRhzgwodlwx5Mg on Jul. 11, 2010.

(Continued)

*Primary Examiner* — Catherine B Kuhlman
(74) *Attorney, Agent, or Firm* — Schwabe Williamson & Wyatt, PC

(57) ABSTRACT

A urinary incontinence device for insertion in a urethra of a user. The device includes a non-absorbent body having an outer surface, the body having a leading end and a trailing end; a removal mechanism having a first end attached to the body and a portion of the removal mechanism located outside the user; a portion of the body having a generally bulbous shape for positioning within the urethra and providing a seal within the urethra preventing urinary leakage from the urethra; and a coating applied to the outer surface of the body for engaging a wall of the urethra and securing the device within the urethra of the user. Another embodiment relates to a method of controlling urinary incontinence comprising: engaging an applicator with the body of the device and introducing into the urethra the device wherein the device is positioned in the user's bulbar urethra.

25 Claims, 15 Drawing Sheets

(56) References Cited

U.S. PATENT DOCUMENTS

| | | | | |
|---|---|---|---|---|
| 5,090,424 | A * | 2/1992 | Simon et al. | 128/885 |
| 5,140,999 | A * | 8/1992 | Ardito | 128/885 |
| 5,498,252 | A * | 3/1996 | Silber | 604/330 |
| 5,509,427 | A * | 4/1996 | Simon | A61F 2/0009 |
| | | | | 128/885 |
| 5,513,659 | A | 5/1996 | Buuck | |
| 5,630,429 | A | 5/1997 | Dann | |
| 5,671,755 | A * | 9/1997 | Simon | A61F 2/0009 |
| | | | | 128/885 |
| 5,701,914 | A | 12/1997 | Loeffler | |
| 5,752,525 | A * | 5/1998 | Simon et al. | 128/885 |
| 5,759,194 | A * | 6/1998 | Hammerslag | 606/214 |
| 5,884,629 | A | 3/1999 | O'Brien | |
| 5,906,575 | A * | 5/1999 | Conway | A61F 2/0022 |
| | | | | 600/29 |
| 5,954,688 | A * | 9/1999 | Adams | A61M 25/0119 |
| | | | | 604/218 |
| 5,971,967 | A * | 10/1999 | Willard | A61M 25/04 |
| | | | | 600/29 |
| 5,989,230 | A * | 11/1999 | Frassica | A61F 2/94 |
| | | | | 600/109 |
| 6,080,142 | A * | 6/2000 | Sachse | A61F 2/0027 |
| | | | | 604/102.01 |
| 6,558,370 | B2 | 5/2003 | Moser | |
| 6,695,763 | B2 * | 2/2004 | Zunker et al. | 600/29 |
| 6,911,001 | B2 * | 6/2005 | Zunker | 600/29 |
| 7,108,655 | B2 * | 9/2006 | Whalen et al. | 600/29 |
| 7,255,673 | B2 * | 8/2007 | Ulmsten | A61B 1/32 |
| | | | | 600/29 |
| 7,655,021 | B2 * | 2/2010 | Brasington et al. | 606/192 |
| 7,771,344 | B2 * | 8/2010 | Ziv | 600/29 |
| 2004/0122285 | A1 * | 6/2004 | Zunker | A61F 2/005 |
| | | | | 600/30 |
| 2006/0079835 | A1 * | 4/2006 | Frassica | 604/93.01 |
| 2006/0195006 | A1 * | 8/2006 | Daurelle et al. | 600/29 |
| 2007/0078389 | A1 * | 4/2007 | Whalen et al. | 604/103.01 |
| 2008/0009931 | A1 * | 1/2008 | Bartning et al. | 623/1.1 |
| 2009/0203959 | A1 * | 8/2009 | Ziv | A61F 2/0009 |
| | | | | 600/29 |

FOREIGN PATENT DOCUMENTS

| | | |
|---|---|---|
| EP | 0821919 A2 | 2/1998 |
| WO | 9219192 A1 | 11/1992 |

OTHER PUBLICATIONS

Datamonitor, "Pipeline and Commercial Insight: Urinary Incontinence," 185 pages, published Dec. 2007.

\* cited by examiner

URINARY INCONTINENCE DEVICE

RELATED APPLICATIONS

This application claims the benefit of U.S. Provisional Patent Application No. 61/229,432, filed on Jul. 29, 2009, which is hereby incorporated by reference in its entirety.

TECHNICAL FIELD

The present disclosure relates to a device for controlling or mitigating urinary leakage associated with urinary incontinence and the methods associated with the use of same.

BACKGROUND

Urinary incontinence is a condition associated with an involuntary leakage of urine. Urinary incontinence affects over 10% of the human population either temporarily or permanently. Urinary incontinence is often a symptom of or results from an underlying medical condition. Both males and females can suffer from urinary incontinence.

Urinary incontinence can be a distressing and embarrassing condition, often having a profound impact on an affected individual's quality of life. Further, urinary incontinence may also affect an individual's self-esteem and disrupt the individual's ability to participate in recreational activities.

Urinary incontinence is often associated with the need for individuals to wear diapers or absorbent pads in order to prevent the individual's clothes from becoming urine-soaked and from smelling of urine. However, there are many drawbacks to such diapers or pads, including the following: (a) the diapers and pads can be bulky, cumbersome and uncomfortable to wear; (b) the diapers and pads can develop unpleasant odors after a short period of time, causing distress and embarrassment to the individual; (c) the diapers and pads may be visible to others, causing the individual to be self-conscious and embarrassed; (d) the diapers and pads can be a significant financial cost to the individual over time; and (e) there may be environmental impacts associated with use and disposal of such diapers and pads. Instead of diapers, rubber pants have been used by individuals suffering from urinary incontinence, but such pants seldom keep clothing from getting wet or smelling of urine.

Alternatives to diapers, absorbent pads and rubber pants include catheters and drainage containers; however, these can be uncomfortable and cumbersome for the individual and cause distress and embarrassment as such devices are visible to others. Further, catheters can be particularly problematic. The drain tubes of catheters extend from the bladder to outside an individual wearer's body via the inside of the urethra and exit through the urethral meatus to the outside of the individual's body. This route of the drain tube can cause significant chaffing and inflammation in an individual's surrounding flesh at the urethral meatus whenever the individual attempts much movement. Thus, catheters and drainage containers can be prohibitive to an individual's quality of life and can be limiting to both an individual's activities and general mobility.

Alternative solutions have included devices to be worn externally by individuals suffering from urinary incontinence, such as a clamp type closure at the exit of the urethral meatus or a wide elastic type strangler. These devices, however, are uncomfortable and can be limiting on an individual's activities.

Some examples of devices designed to block the urethra are disclosed in U.S. Pat. No. 5,671,755, U.S. Pat. No. 4,457,299, U.S. Pat. No. 5,090,424, and European Patent Application No. 8,630,1429.6.

There is a need for a urinary incontinence device that can be easily purchased and that is uncomplicated and user-friendly. Such a urinary incontinence device should allow a user to have a normal quality of life and not be hindered by urinary leakage.

SUMMARY OF THE INVENTION

The embodiments of the present invention relate to a device for controlling or mitigating urinary leakage associated with urinary incontinence and the methods associated with the use of same.

One exemplary embodiment relates to a urinary incontinence device for insertion in a urethra of a user. The device includes a non-absorbent body having an outer surface, and the body having a leading end and a trailing end; a removal mechanism having a first end attached to the body and a portion of the removal mechanism located outside the user; a portion of the body having a generally bulbous shape for positioning within the urethra and providing a seal within the urethra preventing urinary leakage from the urethra; and a coating applied to the outer surface of the body for engaging a wall of the urethra and securing the device within the urethra of the user.

According to one aspect, the device further comprises a groove extending along a length of said leading end of said body.

According to another aspect, the device further comprising an applicator for inserting said device within said urethra. According to a further aspect, the applicator having a channel extending along its length for engaging the removal mechanism.

According to another aspect, the applicator having a first end for engaging the trailing portion of the body. According to a further aspect the trailing end further comprises a socket for engaging the first end of the applicator.

According to another aspect, the removal mechanism further comprising a holding member at a second end of the removal mechanism. According to a further aspect, the applicator engaging the removal mechanism within the channel extending along a length of the applicator and the applicator having a second end for engaging the holding member.

According to another aspect, the coating is selected from the group comprising latex, silicone and combinations thereof.

According to another aspect, the urinary incontinence device is single use. According to a further aspect, the device is reusable.

According to another aspect, the leading end of the device is tapered to permit insertion of the device into the urethra.

Another embodiment relates to a method of controlling urinary incontinence comprising: a) engaging a first end of an applicator with the trailing end of the urinary incontinence device wherein the removal mechanism extends along a length of the applicator; and b) introducing into the urethra the urinary incontinence device, wherein the device is positioned in the user's bulbar urethra.

Another embodiment relates to a urinary incontinence device wherein the leading end, the trailing end and the portion are removably coupled to one another and when assembled form the body of the device.

BRIEF DESCRIPTION OF THE DRAWINGS

The following figures set forth embodiments in which like reference numerals denote like parts. Embodiments are illustrated by way of example and not by way of limitation in the accompanying figures.

DETAILED DESCRIPTION OF THE INVENTION

Embodiments of the present invention relate to a device for controlling or mitigating urinary leakage associated with urinary incontinence and the methods associated with the use of same.

In one embodiment, the device can be used by both males and females suffering from urinary incontinence. The device, when inserted through a person's urethral meatus or external urethral orifice into the urethral canal, blocks urine present in urethral canal from exiting the person's body thereby preventing urinary leakage from the person's urinary drainage system onto his/her clothing or his/her external body parts.

The device prevents urinary leakage throughout the day and night and only needs to be removed for the user to urinate. The same device, in one embodiment, may be reusable and can be used by a user for more than twenty consecutive months, with an average of at least about five insertions and removals each day. The device can be repeatedly inserted and removed throughout the day and night with no discomfort, soreness or inflammation. In an alternative embodiment, the device may be disposable and intended for a single use.

Figure 1:
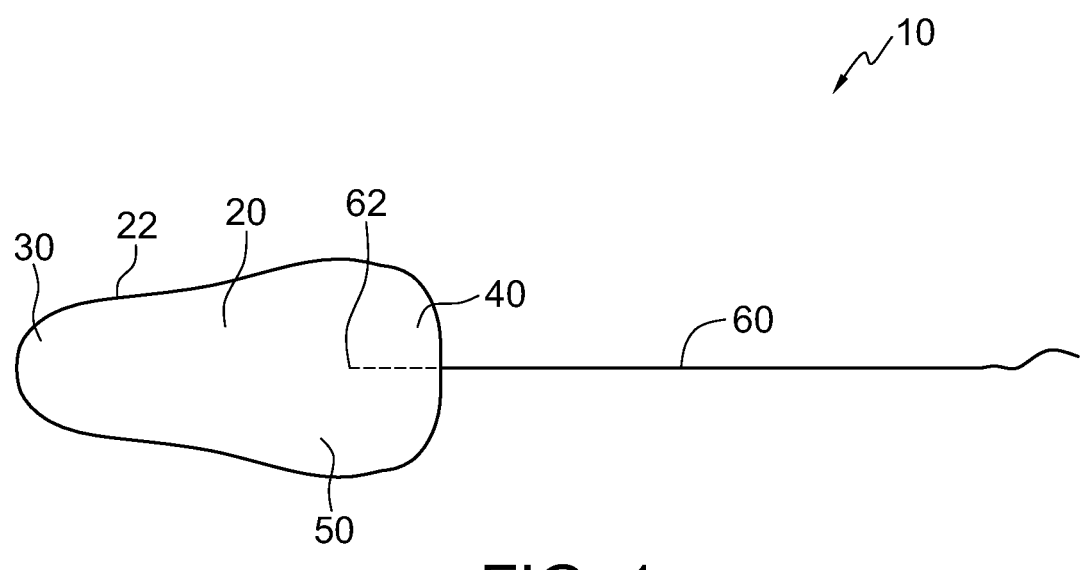
FIG. 1 is a side view of the device.

With reference to FIG. 1, a side view of one embodiment of the urinary incontinence device is provided and indicated by reference number 10. Device 10 comprises a body 20 having a leading end 30 and a trailing end 40. In one embodiment, leading end 30 is tapered for ease of insertion. Body 20 has a portion 50 located between the leading end 30 and trailing end 40, which has a generally bulbous and curved shape. Portion 50 has a generally larger diameter than leading end 30 and trailing end 40. Device 10 further comprises a removal mechanism 60 securely attached to body 20 to facilitate the removal of device 10 from the urethral canal of the user. A first end 62 of removal mechanism 60 is securely attached to body 20. An applicator, shown in FIG. 6 and indicated by reference number 80, is used for inserting the device 10 into the urethral canal via the urethral meatus.

In an alternative embodiment, trailing end 40 has a diameter similar to portion 50 of body 20. In a further alternative embodiment, leading end 30 has a diameter similar to portion 50 of body 20.

Device 10 may be intended for a single use. Alternatively, device 10 may be reusable.

In one embodiment, body 20 is non-absorbent and is made from a hard material, for example glass, hard rubber, or rigid plastic such that the device 10 does not bend or flex on insertion. Alternatively, body 20 is made from a flexible material and is pliable. Body 20 is not limited to being made of a rigid plastic glass, hard rubber or glass material, it may be constructed from any suitable material. In one embodiment, the body 20 is injection molded and constructed from suitable materials. Body 20 is not limited to being manufactured by injection molding. Body 20 may be manufactured by any suitable method.

The outer surface 22 of body 20 is coated with a material that facilitates the anchoring of device 10 in the desired position in the urethral canal of a user. The material of the outer surface 22 of body 20 is preferably a material that enables the development of friction between the wall of the urethra and the outer surface 22 of body 20 to assist in maintaining the device 10 in the proper position within the urethral canal. Further, the material is preferably one that prevents the outer surface 22 of body 20 from becoming attached to the wall of the urethra and is biocompatible and biologically inert. In one embodiment, the outer surface 22 of body 20 is coated with latex. The coating material is not limited to latex, the coating material may be any suitable material for example, silicone. A person skilled in the art would understand that other biologically inert, friction materials would also be suitable to coat the outer surface of body 20.

When body 20 is positioned in the desired location in the urethral canal of a user, body 20 provides a seal in the urethral canal to prevent urinary leakage from the urethra.

Portion 50 of body 20 is slightly larger in diameter than the relaxed, internal diameter of the urethral canal. The size of body 20 may be customized for each user and may be further customized depending on the gender of the user. In one embodiment, portion 50 is preferably from between about 3 mm and about 15 mm in diameter, more preferably from between about 5 mm and about 15 mm, more preferably from between about 8 mm and about 15 mm, and even more preferably from between about 10 mm and about 13 mm. In an alternative embodiment, the diameter of portion 50 is one of about: 3 mm, 4 mm, 5 mm, 6 mm, 7 mm, 8 mm, 9 mm, 10 mm, 11 mm, 12 mm, and 13 mm. The wall of the urethral canal is flexible and can stretch to accommodate portion 50 on insertion of device 10. The additional tension of the wall of the urethral canal around portion 50 of body 20 further holds and secures body 20 in the proper position within the urethral canal. It will be appreciated that the portion 50 may be any suitable size or shape.

In one embodiment, removal mechanism 60 is preferably a strong, durable string, cord, lanyard, thread or ribbon capable of being sanitized, such as 49-strand stainless steel cable. A person skilled in the art would understand that the removal mechanism may be constructed from any other suitable strong, durable material.

In one embodiment, when device 10 is properly positioned in the urethral canal of a user, removal mechanism 60 has a length that extends beyond the urethral canal, exterior to the urethral meatus. This length is preferably from between about 100 mm and about 200 mm, more preferably from between about 125 mm and about 175 mm, and even more preferably from between about 135 mm and about 160 mm. It will be appreciated that the removal mechanism 60 may be any suitable length.

Figure 2:
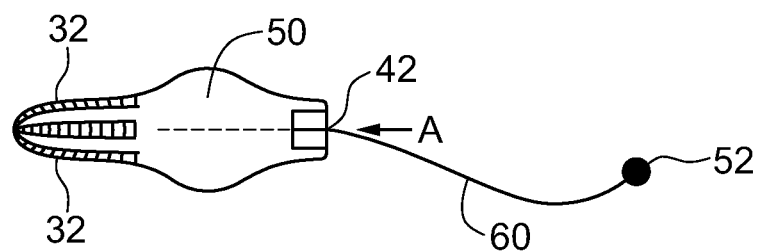
FIG. 2 is a side view of another embodiment of the device.

FIG. 2 shows another embodiment of the device, wherein leading end 30 of body 20 comprises a groove 32 extending along the length of the leading end 20. Groove 32 is provided for receiving lubricant applied to device 10 upon insertion of the device 10 in the urethral canal. Groove 32 helps in limiting the smearing or spreading of lubricant to portion 50 and trailing end 40. In one embodiment, the second end 64 of removal mechanism 60 is secured to a holding member 52. Holding member 52 is designed to be easily to grasped by the user. Holding member 52 is a round bead made from glass. The holding member 52 may alternatively be a small ball, a loop, a cube or any similar secured attachment that is easy to grasp. Holding member 52 is made of glass and is rigid. The holding member 52 may alternatively be flexible and deform when pressure is applied. The holding member 52 is not limited to being made of glass, it may be constructed from any suitable material. Holding member 52 serves to provide a place or point where a user can grasp the removal mechanism 60 when they are ready to remove device 10 from the urethral canal. The holding member 52 is sized for a comfortable fit near the users urethral meatus. It will be appreciated that the holding member 52 may be any suitable size or shape.

Figure 3:
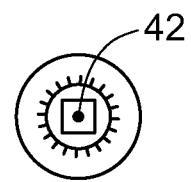
FIG. 3 is a view on "A" of the device of FIG. 2.

With reference to FIG. 3, a view of trailing end 40 comprising a recess 42 is shown. Removal mechanism 60 extends from recess 42 of trailing end 40. In one embodiment, recess 42 is preferably a shallow socket for securely engaged with applicator 80 when inserting device 10 into the urethral canal. In one embodiment, recess 42 is a shallow square socket. Recess 42 may alternatively be rectangular, ovular and circular. It will be appreciated by a person skilled in the art that the recess 42 may be any suitable size or shape.

Figure 4:
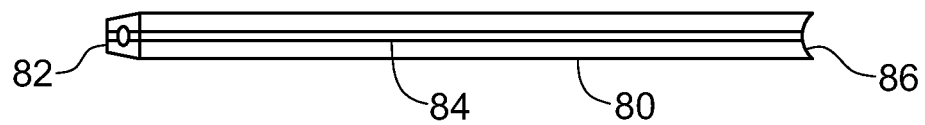
FIG. 4 is a side view of an applicator for inserting the device into the urethral canal.

With reference to FIG. 4, an applicator for use in inserting body 20 into the urethral canal via the urethral meatus is shown and indicated by reference number 80. Applicator 80 is an elongate rod for inserting body 20 into the urethral canal of a female or male. Applicator 80 comprises a first end 82 for engaging with recess 42 of trailing end 40 of body 20, and a second end 86. In one embodiment, applicator 80 is a hollow tube through which removal mechanism 60 can be thread, or passed therethrough. In an alternative embodiment, applicator 80 comprises a channel 84 extending along the length of applicator 80 to engage removal mechanism 60.

In a further embodiment, second end 86 of applicator 80 is shaped to receive holding member 52. When holding member 52 is received at second end 86 of applicator 80, the removal mechanism is stretched taunt along the length of applicator 80.

Figure 5:
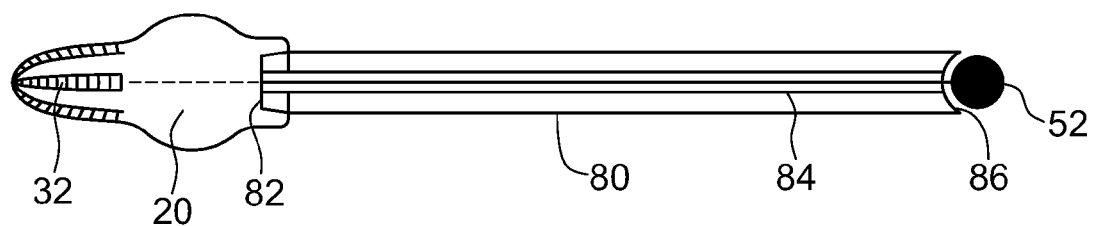
FIG. 5 is a side view of the device of FIG. 2 wherein the applicator of FIG. 4 is engaged therewith.

Referring to FIG. 5, a side view of body 20 removably engaged with applicator 80 and removal mechanism 60 is provided. When device 10, including removal mechanism 60, is assembled together with applicator 80 prior to insertion of body 20 into the urethral canal, the removal mechanism 60 is positioned within channel 84 of applicator 80 and front end 82 of applicator 80 is fully engaged with recess 42 of trailing end 40. The removal mechanism 60 extends from trailing end 40 along the length of applicator 80 and the holding member 52 is engaged with the second end 86 of applicator 80. When assembled, body 20, removal mechanism 60, holding member 52, and applicator 80 for a single assembly ready for insertion into a user's urethral canal. In one embodiment, the length of applicator 80 and the length of removal mechanism 60 from the point that removal mechanism 60 extends from trailing end 40 are approximately the same length.

It would be appreciated by a person skilled in the art that the leading end 30, trailing end 40 and portion 50 may be removably coupled to form body 20. Alternatively, leading end 30, trailing end 40 and portion 50 maybe permanently affixed to form body 20.

Figure 6:
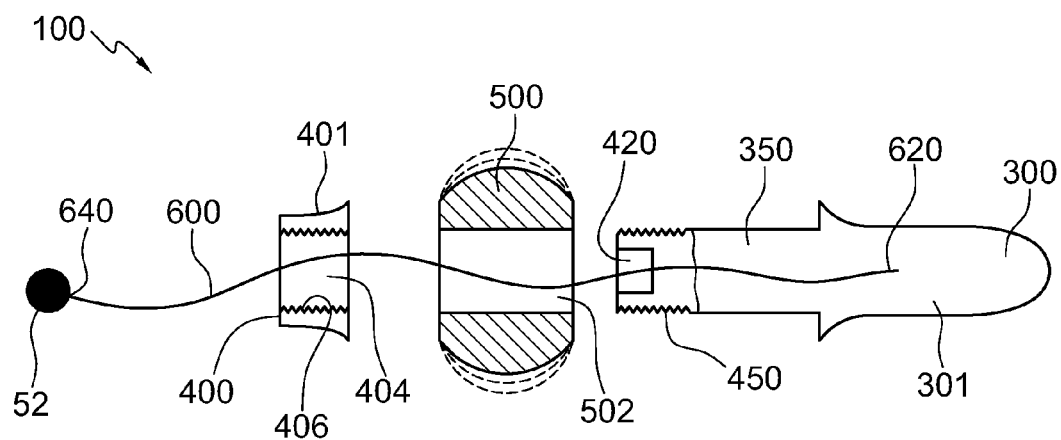
FIG. 6 is a disassembled side view of the device of another embodiment of the device.

Referring to FIG. 6, a disassembled view of another embodiment of a urinary incontinence device 100 is provided. Device 100 comprises body 200 having leading portion 301, trailing portion 401 and central portion 500. Central portion 500 is located between the leading portion 301 and trailing portion 401, and has a generally bulbous and curved shape. Each of the leading portion 301 and trailing portion 401 have diameters that are less than the diameter of bulbous portion 500. The diameter of central portion 500 is preferably from between about 3 mm and about 15 mm in diameter, more preferably from between about 5 mm and about 15 mm, more preferably from between about 8 mm and about 15 mm, and even more preferably from between about 10 mm and about 13 mm. In an alternative embodiment, the diameter of central portion 500 is one of about: 3 mm, 4 mm, 5 mm, 6 mm, 7 mm, 8 mm, 9 mm, 10 mm, 11 mm, 12 mm, and 13 mm. It will be appreciated that the central portion 500 may be any suitable size or shape.

In an alternative embodiment, trailing portion 401 has a diameter similar to central portion 500 of body 200. In a further alternative embodiment, leading portion 301 has a diameter similar to central portion 500 of body 200.

Leading portion 301 comprises a mandril 350 extending from the end distal to leading end 301. Central portion 500 defines a passageway 502 for receiving mandril 350. Mandril 350 extends through passageway 502 and securely engages with trailing portion 401. Trailing portion 401 comprises an opening 404 for engaging mandril 350. In one embodiment, mandril 350 comprises threads 450 for securely engaging complementary threads 406 on an inner surface of opening 404 of trailing portion 401. A person skilled in the art would understand that any suitable fastener may be used for securely engaging mandril 350 and trailing portion 401. Alternatively, leading portion 301, central portion 500 and trailing portion 401 may be removably coupled or permanently fixed thereto. Leading portion 301, central portion 500, trailing portion 401 are flush with one other when assembled together and the outer surfaces of the portions form a continuous smooth line.

Device 100 further comprises removal mechanism 600. Removal mechanism 600 is securely attached to leading portion 301 of body 200 and facilitates the removal of device 100 from the urethral canal of the user. Removal mechanism 600 extends from leading portion 301 through the passageway 502 of central portion 500, extends through opening 404 of trailing portion 401. Removal mechanism 600 has a length that extends beyond the trailing portion 401 of device 100.

In one embodiment, when device 100 is assembled and properly positioned in the urethral canal of a user a portion of removal mechanism 600 is positioned within the urethra and a second end 640 of removal mechanism 600 extends outward from the urethral meatus. In one embodiment, second end 640 of removal mechanism 600 is secured to a holding member 700.

In one embodiment, a distal end 352 of mandril 350 comprises a recess 420 for removably engaging with applicator 80 (shown in FIG. 6). In one embodiment, device 100 may be provided in kit form with several different central portions ranging in diameters. This provides a simple, user friendly customization option for a user. A user may select the correctly sized central portion 500 to form the proper fit within his/her urethral canal.

Figure 7:
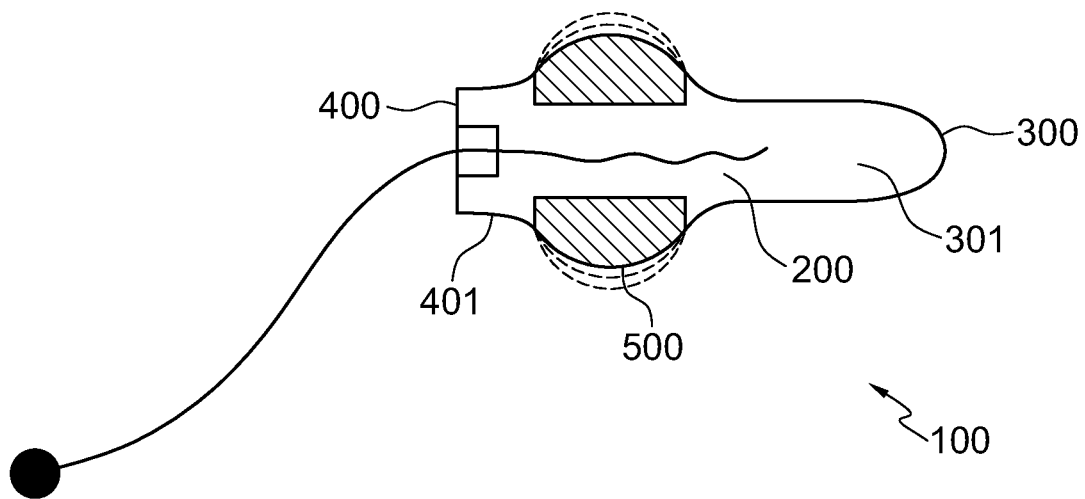
FIG. 7 is a cross-sectional side view of the assembled device of FIG. 6.

Referring to FIG. 7, a side view of the assembled urinary incontinence device 100 of FIG. 6 is provided. Leading portion 301, trailing portion 401, and central portion 500 are assembled and are removable coupled to one another. Leading end 300 is tapered for ease of insertion.

A first end 620 of removal mechanism 600 is secured to leading end 300 of body 200 and extends through trailing portion 401. A portion of removal mechanism 600 is positioned within the urethra and a second end 640 of removal mechanism 600 extends outward from the urethral meatus. Second end 640 of removal mechanism 600 is secured to holding member 52.

Recess 420 is preferably a shallow socket capable of remaining securely engaged with applicator 80 upon rotation and movement of applicator 80 when inserting device 100 into the urethral canal. In one embodiment, recess 420 is a shallow square socket. Recess 420 may alternatively be rectangular, ovular and circular. It will be appreciated by a person skilled in the art that the recess 420 may be any suitable size or shape.

In one embodiment, when device 10 is properly positioned in the urethral canal of a user, removal mechanism 600 has a length that extends beyond the urethral canal, exterior to the urethral meatus. This length is preferably from between about 100 mm and about 200 mm, more preferably from between about 125 mm and about 175 mm, and even more preferably from between about 135 mm and about 160 mm. It will be appreciated that the removal mechanism 60 may be any suitable length.

Figure 8:
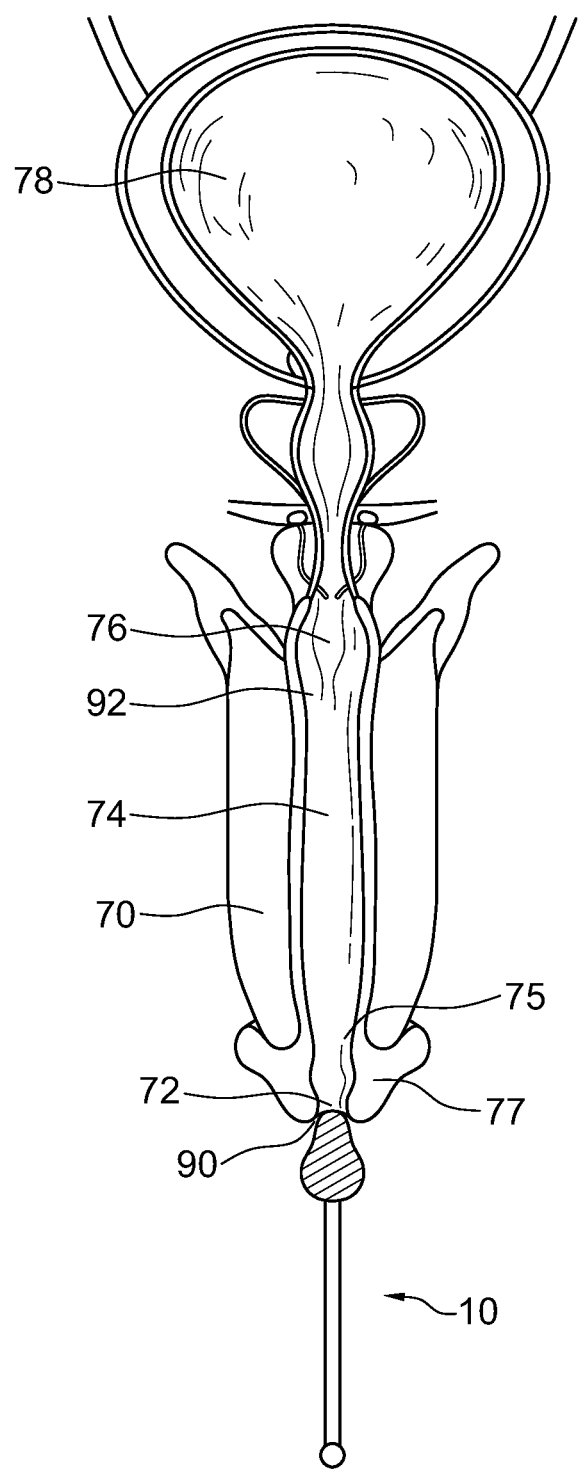
FIG. 8 is a diagrammatic illustration of the insertion of the device in the urethra of a male.
Figure 9:
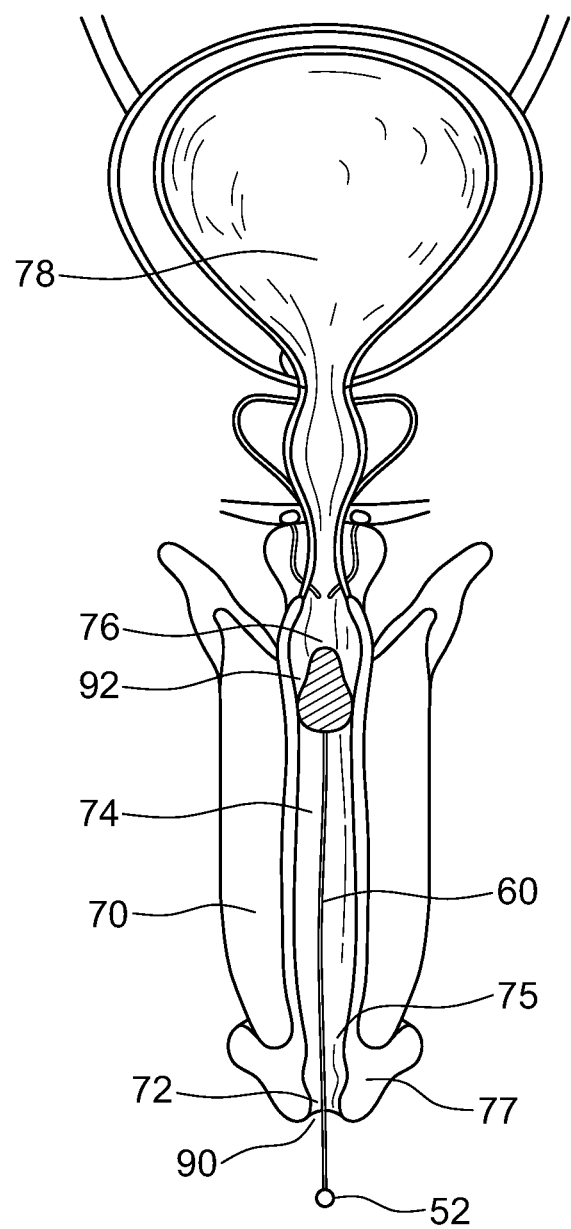
FIG. 9 is a cross-sectional view of the urethra of a male with the device positioned therein.

With reference to FIG. 8, insertion of device 10 into a male user's urethral canal is shown. Upon assembly body 20, removal mechanism 60, holding member 52, and applicator 80, and application of body 20 with a lubricant on the outer surface of leading end 30, the user can grasp the applicator 80 and insert leading end 30 into the urethral canal through the urethral meatus 90. The lubricant is preferably a water-based or water-soluble personal lubricant. A person skilled in the art will understand that any type of personal lubricant that provides low surface tension, has good wetting characteristics and dissipates within the urethral canal can be used to lubricate body 20 prior to insertion. Insertion of body 20 to the proper position is easily accomplished by the user by lightly pushing on the second end 86 of applicator 80 when leading end 30 is abutting the urethral meatus. In one embodiment, the user may use an in-and-out vibratory, reciprocating, short stroke motion together with a continuous clockwise rotation of applicator 80 to facilitate smooth insertion of device 10 into the urethral canal. The proper position for body 20 in the male's urethral canal is in the bulbar urethra 92 of the spongy urethra, as shown in FIG. 9. Body 20 is easily positioned in the bulbar urethra 92. When the user is inserting body 20 up the urethral canal, the user hits an area of diminished resistance, at which point, the user stops pushing applicator 80, disengages holding member 52 from second end 86 of applicator 80, and disengages applicator 80 from recess 42 of trailing end 40 to withdraw applicator 80 from the urethral canal. Once applicator 80 is removed from the urethral canal, body 20, with a portion of removal mechanism 60, is disposed within the bulbar urethra 92 of the urethral canal, and the other portion of removal mechanism 60 and holding member 52 are exposed and extend outward from the urethral meatus 90. At this point, to anchor body 20 in the bulbar urethra 92, the user grasps holding member 52 and pulls slightly move device 10 within the urethral canal until an increase in resistance is felt by the user. The slight withdrawal of device 10 causes the wall of the urethra to gather and fold around device 10, which facilitates the anchoring of device 10 within the bulbar urethra 92. The gathering and folding of the urethral wall around the body 20 of device 10 creates a frictional force between the body and the urethral wall.

Similarly, the removal of device 10 from the urethral canal can be easily done by the user. When the user is ready to remove device 10, the user simply pulls downward on removal mechanism 60 at holding member 52. This action will cause device 10 to be comfortably and easily withdrawn from the urethral canal. The user can re-insert the same device 10 using the method set out above. Prior to re-insertion, device 10 is cleaned with soap and water. Cool tap water is generally sufficient lubrication for re-insertion of device 10; however, a user may re-apply lubricant to body 20 prior to re-insertion.

In the male, as shown in FIG. 9, the device 10 is positioned in the urethral canal 72 in the spongy urethra 74, proximate to the membranous urethra 76, and is well upstream of the urethral meatus 90 and well downstream of the bladder 78 (FIG. 9). The spongy urethra 74 is subdivided into two portions: the bulbar urethra 92 and the penile or pendulous urethra 75. The device 10 is positioned within the bulbar urethra 92 of the spongy urethra 74, wherein the spongy urethra 74 is slightly dilated. The bulbar urethra 92 is enveloped by more developed and posteriorly located spongy tissue as compared to the penile urethra 75, where the spongy tissue is relatively minimal and symmetrically surrounds the penile urethra 75. The bulbar urethra 92 lies between the membranous urethra 76 and the penile urethra 75. The penile urethra 75 extends from the glans penis 77, which is proximate to the urethral meatus 90, to the suspensory ligament, from which the bulbar urethra 92 extends. When properly positioned in the bulbar urethra 92 portion of the spongy urethra 74, the device 10 does not allow any leakage of urine beyond the device 10 itself.

With reference to FIG. 9, device 10 is shown positioned in the bulbar urethra 92 of the spongy urethra in a male. It should be noted that when device 10 is properly positioned in the bulbar urethra 92 of the urethral canal, only removal mechanism 60 and holding member 52 will be exposed and extend outward from the urethral meatus 90.

Together the material on the outer surface of body 20, with the diameter of bulbous region 50, the correct positioning of body 20 within the bulbar urethra 92 and the folds in the wall of the urethra, secure and seal body 20 in the urethral canal to effectively prevent urinary leakage. The device may be for single use, may be reusable, and may be sold in kit form and further include an applicator and lubricant. The device may be available in multiple sizes and/or the bulbous region of the device may be provided in different sizes.

Figure 10:
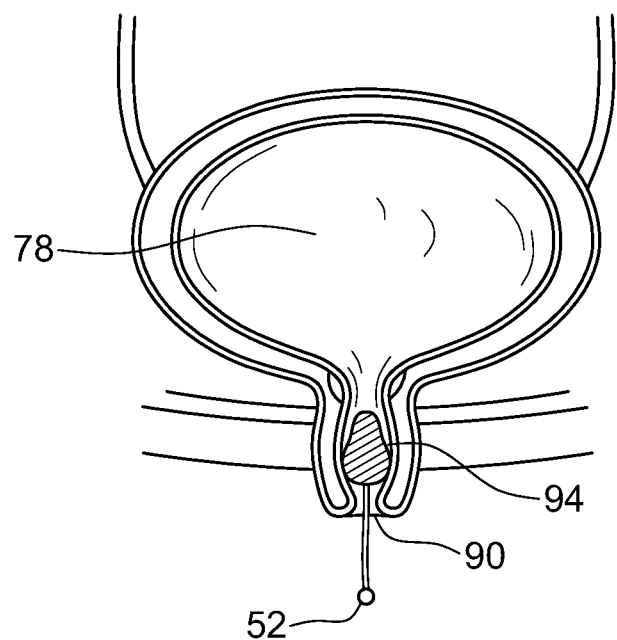
FIG. 10 is a cross sectional view of the urethra of a women with the device positioned therein.
Figure 11:
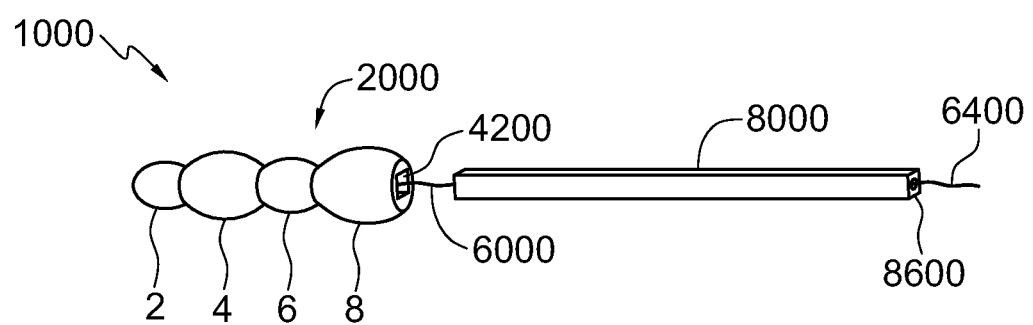
FIG. 11 is a side perspective view of another embodiment of the device prior to engagement with the applicator of FIG. 6.

Referring to FIG. 10, device 10 is shown positioned in the urethral canal 94 in a female. As in the male, when device 10 is properly positioned in the urethral canal 94, only removal mechanism 60 and holding member 52 will be exposed and extend outward from the urethral meatus 90.

Figure 12:
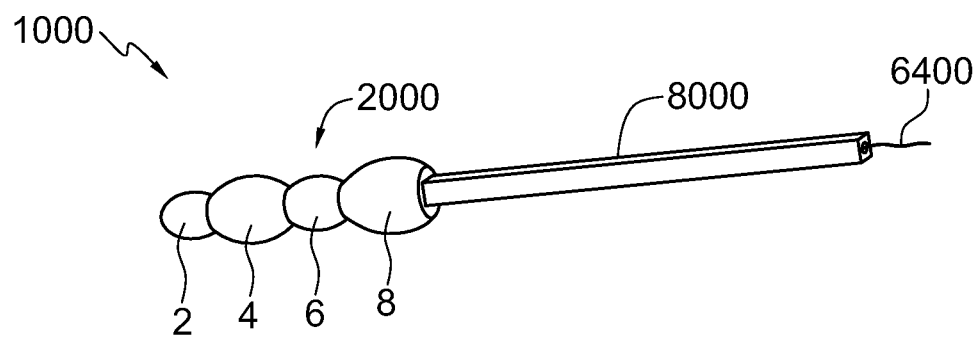
FIG. 12 is a side perspective view of the device of FIG. 11 wherein the applicator of FIG. 6 is engaged therewith.
Figure 13:
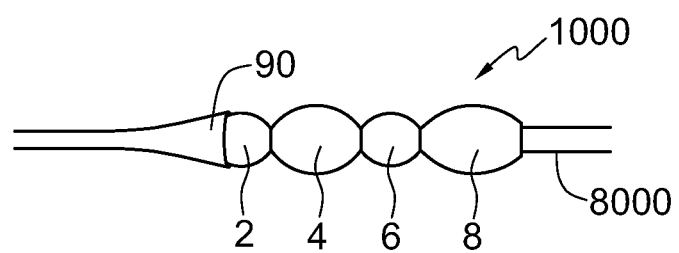
FIG. 13 is a side perspective view of the device and applicator of FIG. 12 wherein the device is positioned to be inserted in the urethra meatus of a user.
Figure 14:
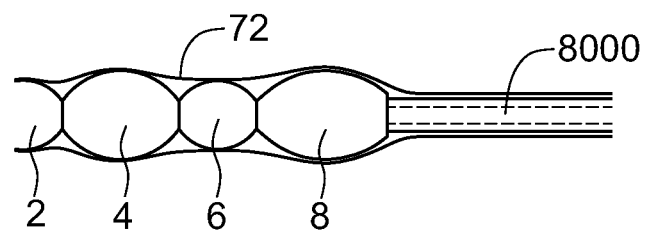
FIG. 14 is a side perspective view of the urethra of a user, wherein the device and applicator of FIG. 12 are being inserted in the spongy urethra of the urethral canal.
Figure 15:
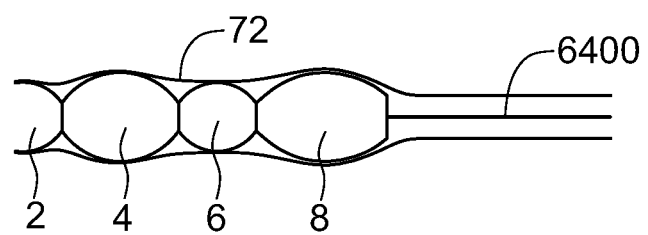
FIG. 15 is a side perspective view of the urethral canal of a user, wherein the device of FIG. 12 is positioned therein.

Referring to FIGS. 11 through 15, another embodiment of the urinary incontinence device is provided and indicated by reference number 1000. Device 1000 comprises a body 2000 having first portion 2, a second portion 4, a third portion 6 and a forth portion 8. Each of the first 2, second 4, third 6, and fourth 9 portions have a generally bulbous and curved shape. Further, device 1000 includes removal mechanism 6000 securely attached to body 2000 to facilitate removal of device 1000 from the urethral canal of a user. Removal mechanism 6000 is securely attached to the fourth portion 8 of body 2000. Recess 4200 is provided on the distal end of the fourth portion 8 to removably engage with applicator 8000. Removal mechanism 6000 extends from the fourth portion 8 and along the length of applicator 8000. Second end 6400 of removal mechanism 6000 exits applicator 8000 from the second end 8600 of applicator 8000. FIG. 12 shows device 1000 engaged with applicator 8000, prior to insertion into a user's urethral canal. FIG. 13 shows the initial step of gently pushing device 1000 through the urethral meatus and into the urethral canal. FIG. 14 illustrates the positioning of device 1000 in the spongy urethra of a male's urethral canal using applicator 8000. FIG. 15 shows device 1000 properly positioned in the urethral canal of a user with the applicator 8000 removed from device 1000.

By using the device, a user can lead a normal lifestyle and can participate in any type of recreational activity, including walking, running, biking and swimming, without the discomfort of being in wet, urine-smelling clothing. The device is not limiting on a user's mobility and is not uncomfortable to wear. The presence of the device in the urethral canal is imperceptible to a user and is not visible to others.

The device is simple in design and can be inserted by the user without any assistance from others. Insertion and removal of the device is easy and straightforward. When a user needs to relieve his/her bladder, the device is easily removed and can be washed with soap and water prior to re-insertion. The whole process of removing the device, urinating and re-inserting a cleaned device takes less than about four minutes.

While preferred embodiments of the present invention have been shown and described herein, it will be obvious to those skilled in the art that such embodiments are provided by way of example only. Numerous variations, changes, and substitutions will be obvious to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

I claim:

1. A method for using a device in the treatment of urinary incontinence in a male user, comprising:
    engaging the device with an applicator;
    while holding the applicator, inserting a leading portion of the device through a urethral orifice into a urethral canal of the male user;
    advancing the applicator to move the device into the urethral canal;
    stopping advancing the applicator when an area of diminished resistance is reached prior to the device reaching the user's bladder;
    withdrawing the applicator from the urethral canal; and
    pulling a holding member of the device until an increase in resistance is detected to secure the device within the user's urethra;
    wherein the device comprises:
    a non-absorbent body having an outer surface, said body having the leading portion including a proximal end of said body, a trailing portion including a distal end of said body, and a central portion disposed between the leading portion and the trailing portion, said leading portion, trailing portion and central portion included in a unitary body, and wherein the leading portion is shaped to spread tissue upon insertion in a penis of the male user; and
    a removal mechanism having a first end attached to the body, wherein, when the device is in situ, a portion of said removal mechanism is located outside the user, and wherein the removal mechanism, at a distal end, comprises the holding member;
    wherein:
    a maximum diameter of the leading portion is less than a maximum diameter of the central portion, and a maximum diameter of the trailing portion is less than the maximum diameter of the central portion,
    the maximum diameter of the central portion is larger than a relaxed internal diameter of a user's urethral canal,
    a shape of the body enables positioning the body within the user's urethra when the device is in situ, such that the entire body is retained within the user's urethra,
    the outer surface of the body is comprised of a material enabling the development of friction between the outer surface and a wall of the user's urethra, when the device is in situ, to maintain position of the device, and
    said removal mechanism is shaped for engaging an applicator.

2. The method of claim 1, further comprising:
    prior to inserting the leading portion of the device through the urethral orifice into the urethral canal of the male user, supplying a lubricant at the proximal end of said body.

3. The method of claim 1, wherein advancing the applicator comprises rotating the applicator.

4. The method of claim 1 wherein the outer surface of said body comprises a coating adapted to engage a wall of the urethra and to secure said device within the urethra.

5. A urinary incontinence device for use in a male user, the device comprising:
    a non-absorbent body having a smooth outer surface, said body having a leading portion including a proximal end of said body, a trailing portion including a distal end of said body, and a central portion disposed between the leading portion and the trailing portion, the central portion having a fixed bulbous shape, said leading portion, trailing portion and central portion included in a unitary body, and wherein the leading portion is shaped to spread tissue upon insertion in a penis of the male user; and
    a removal mechanism having a first end attached to the body, wherein, when the device is in situ, a portion of said removal mechanism is located outside the user, and wherein the removal mechanism, at a distal end, comprises a holding member;

wherein:
a maximum diameter of the leading portion is less than a maximum diameter of the central portion, a maximum diameter of the trailing portion is less than the maximum diameter of the central portion, and the maximum diameter of the leading portion is less than the maximum diameter of the trailing portion,
the maximum diameter of the central portion is larger than a relaxed internal diameter of a user's urethral canal,
the length of the leading portion is greater than the length of the trailing portion,
a shape of the body enables positioning the body within the user's urethra when the device is in situ, such that the entire body is retained within the user's urethra, to restrict urine flow within the urethra past the urinary incontinence device,
the outer surface of the body is comprised of a material enabling the development of friction between the outer surface and a wall of the user's urethra, when the device is in situ, to maintain position of the device, and
said removal mechanism is shaped for engaging an applicator.

6. The urinary incontinence device according to claim 5, wherein said device further comprises the applicator, wherein the applicator is configured for inserting said device within the user's urethra.

7. The urinary incontinence device according to claim 6, wherein said applicator has an open channel extending along, and open along, its entire length for retaining a portion of said removal mechanism during insertion.

8. The urinary incontinence device according to claim 6, wherein said applicator is hollow and at least a portion of said removal mechanism is disposed therein when the device and the applicator are engaged.

9. The urinary incontinence device according to claim 6, wherein said applicator has an end for engaging said holding member.

10. The urinary incontinence device of claim 6, wherein the applicator does not compress the device when the applicator and the device are engaged.

11. The urinary incontinence device according to claim 5, wherein said outer surface comprises a biologically inert material.

12. The urinary incontinence device of claim 5, wherein the outer surface of the body comprises a coating adapted to engage a wall of said urethra to secure said device within the urethra.

13. The urinary incontinence device according to claim 5, wherein said device further comprises a groove recessed in and along the body and extending from the proximal end of the body along the leading portion of said body and configured to receive lubricant.

14. The urinary incontinence device according to claim 5, wherein said device is single use.

15. The urinary incontinence device according to claim 5, wherein said device is reusable.

16. The urinary incontinence device of claim 5, wherein the outer surface of the body comprises latex or silicone.

17. The urinary incontinence device of claim 5, wherein the body, the removal mechanism, and the holding member are unitary and permanently affixed together, and each comprise a biologically inert material.

18. The urinary incontinence device of claim 5, wherein the leading portion tapers from the central portion to the proximal end of the body, and wherein the trailing portion tapers from the central portion to the distal end of the body.

19. The urinary incontinence device according to claim 5, wherein said body comprises a material selected from the group consisting of rubber, plastic, and glass.

20. The urinary incontinence device according to claim 5, wherein the body is dimensioned so as to be completely contained within the user's body when the device is in situ.

21. The urinary incontinence device according to claim 5, wherein the body does not bend or flex.

22. The urinary incontinence device according to claim 5, wherein the body is non-hollow.

23. The urinary incontinence device according to claim 5, wherein the fixed bulbous central portion has a fixed maximum diameter of 8 to 15 mm.

24. The urinary incontinence device according to claim 5, wherein the length of the leading portion is greater than the length of the central portion.

25. The urinary incontinence device according to claim 5, wherein the maximum diameter of the trailing portion is greater than a maximum diameter of the removal mechanism.

* * * * *